United States Patent
Belson

(10) Patent No.: US 8,281,786 B2
(45) Date of Patent: Oct. 9, 2012

(54) RESPIRATORY SYSTEM FOR INDUCING THERAPEUTIC HYPOTHERMIA

(75) Inventor: Amir Belson, Los Altos, CA (US)

(73) Assignee: Thermocure, Inc., Los Altos, CA (US)

( * ) Notice: Subject to any disclaimer, the term of this patent is extended or adjusted under 35 U.S.C. 154(b) by 1002 days.

(21) Appl. No.: 12/269,009

(22) Filed: Nov. 11, 2008

(65) Prior Publication Data

US 2009/0107491 A1    Apr. 30, 2009

Related U.S. Application Data

(63) Continuation of application No. 10/587,103, filed as application No. PCT/US2005/002600 on Jan. 24, 2005, now Pat. No. 8,100,123.

(60) Provisional application No. 60/538,789, filed on Jan. 22, 2004.

(51) Int. Cl.
*A62B 7/02* (2006.01)
*F24F 6/14* (2006.01)

(52) U.S. Cl. ......... 128/204.15; 128/203.15; 128/204.18; 128/200.24; 604/24

(58) Field of Classification Search ............. 128/203.12, 128/203.15, 203.16, 203.25, 203.26, 203.27, 128/203.29, 204.14, 204.17, 204.18, 204.23, 128/205.11, 205.25; 607/96, 105, 113
See application file for complete search history.

(56) References Cited

U.S. PATENT DOCUMENTS

| | | |
|---|---|---|
| 4,711,375 A | 12/1987 | Mader et al. |
| 5,755,756 A | 5/1998 | Freedman, Jr. et al. |
| 6,149,624 A | 11/2000 | McShane |
| 6,244,052 B1 | 6/2001 | Kasza |
| 6,303,156 B1 | 10/2001 | Ferrigno |
| 6,547,811 B1 | 4/2003 | Becker et al. |
| 6,572,638 B1 | 6/2003 | Dae et al. |
| 6,582,457 B2 | 6/2003 | Dae et al. |
| 2003/0066304 A1 | 4/2003 | Becker et al. |
| 2003/0131844 A1 | 7/2003 | Kumar et al. |

(Continued)

FOREIGN PATENT DOCUMENTS

EP    0 206 982 A1    12/1986

(Continued)

OTHER PUBLICATIONS

Supplementary European Search Report of European Patent Application No. 05712159.2, mailed Oct. 13, 2010, 3 pages total.

(Continued)

*Primary Examiner* — Lynne Anderson
*Assistant Examiner* — Kathryn D Sheikh
(74) *Attorney, Agent, or Firm* — Wilson, Sonsini, Goodrich & Rosati

(57) ABSTRACT

The present invention provides a method and apparatus for controlling a patient's body temperature and in particular for inducing therapeutic hypothermia. Various embodiments of the system are described. The system includes: a source of breathing gas, which may be in the form of a compressed breathing gas mixture; a heat exchanger or other heating and/or cooling device; and a breathing interface, such as a breathing mask or tracheal tube. Optionally, the system may include additional features, such as a mechanical respirator, a nebulizer for introducing medication into the breathing gas, a body temperature probe and a feedback controller. The system can use air or a specialized breathing gas mixture, such as $He/O_2$ or $SF/O_2$ to increase the heat transfer rate. In addition, the system may include an ice particle generator for introducing fine ice particles into the flow of breathing gas to further increase the heat transfer rate.

23 Claims, 4 Drawing Sheets

U.S. PATENT DOCUMENTS

| | | |
|---|---|---|
| 2003/0136402 A1 | 7/2003 | Jiang et al. |
| 2005/0042170 A1 | 2/2005 | Jiang et al. |
| 2005/0279108 A1 | 12/2005 | Akselband et al. |

FOREIGN PATENT DOCUMENTS

| | | |
|---|---|---|
| JP | 03-505190 | 12/2003 |
| WO | WO 99/66938 A1 | 12/1999 |
| WO | WO 00/18459 A1 | 4/2000 |
| WO | WO 01/08593 A1 | 2/2001 |
| WO | WO 03/047603 A2 | 6/2003 |
| WO | WO 03/059425 A1 | 7/2003 |
| WO | WO 2005/113046 A2 | 12/2005 |
| WO | WO 2005/113046 A3 | 3/2007 |

OTHER PUBLICATIONS

Belson, Amir, U.S. Appl. No. 10/587,103 entitled, "Respiratory system for inducing therapeutic hypothermia," filed Jul. 21, 2006.

U.S. Appl. No. 13/326,101, filed Dec. 14, 2011, Belson.

Pogonip in Pittsburg air. Weather man there says it's death from frozen fog. New York Times. Jan. 12, 1910.

International search report dated Sep. 8, 2005 for PCT/US2005/002600.

RESPIRATORY SYSTEM FOR INDUCING THERAPEUTIC HYPOTHERMIA

CROSS-REFERENCE TO RELATED APPLICATIONS

This application is a continuation of U.S. application Ser. No. 10/587,103, filed Jul. 9, 2008 now U.S. Pat. No. 8,100,123; which is the National Stage of International Application No. PCT/US2005/002600, filed Jan. 24, 2005; which application claims the benefit of U.S. Provisional Application No. 60/538,789, filed Jan. 22, 2004. These applications are incorporated by reference in their entirety as if fully set forth herein.

FIELD OF THE INVENTION

The present invention relates generally to apparatus and methods for selective modification and control of a patient's body temperature. More particularly, it relates to a respiratory system and methods for raising and lowering a patient's body temperature by heat exchange with the patient's lungs. The respiratory system provides rapid induction of therapeutic hypothermia by having the patient breathe a respiratory gas that carries with it ice particles or a frozen mist to enhance heat capacity. The respiratory gas may be air or a special gas mixture that includes oxygen (about 20% concentration or more) and a gas with a high heat capacity (Cp) for more effective heat exchange, such as helium or sulfur hexafluoride.

BACKGROUND OF THE INVENTION

The respiratory system of the present invention is useful for treating patient's with hypothermia or hyperthermia and for inducing therapeutic hypothermia for treating a variety of conditions, including acute myocardial infarction and emergent stroke.

Man is considered to be a tropical animal. Normal functioning of the human animal requires a body temperature of approximately 37 degrees Celsius (98.6 degrees Fahrenheit). The body can self-compensate for small upward or downward variations in temperature through the activation of a built-in thermoregulatory system, controlled by temperature sensors in the skin. The response to an upward variation in body temperature is the initiation of perspiration, which moves moisture from body tissues to the body surface. When the moisture reaches the surface it evaporates, carrying with it a quantity of heat. The explanation for a person becoming thirsty when exposed to a hot environment for a period of time is that fluids lost due to perspiration must be replaced. The response to a downward variation in body temperature is shivering, which is the body's attempt to generate heat. Shivering is an involuntary contraction and expansion of muscle tissue occurring on a large scale. This muscle action creates heat through friction.

Hypothermia is defined as a core temperature of less than 35 degrees Celsius. Hypothermia is also considered the clinical state of subnormal temperature when the body is unable to generate sufficient heat to effectively maintain functions. Many variables contribute to the development of hypothermia. Age, health, nutrition, body size, exhaustion, exposure, duration of exposure, wind, temperature, wetness, medication and intoxicants may decrease heat production, increase heat loss, or interfere with thermostability. The healthy individual's compensatory responses to heat loss via conduction, convection, radiation, evaporation and respiration may be overwhelmed by exposure. Medications may interfere with thermoregulation. Acute or chronic central nervous system processes may decrease the effectiveness of thermoregulation.

Mild Hypothermia is when the core temperature is 34-35 degrees Celsius. The patient is still alert and able to help him/herself and intense shivering begins. The patient's movements, however, become less coordinated and the coldness creates some pain and discomfort.

Moderate Hypothermia is when the patient's core temperature is 31-33 degrees Celsius. Shivering slows or stops, muscles begin to stiffen and mental confusion and apathy sets in. Speech becomes slow, vague and slurred, breathing becomes slow and shallow, and drowsiness and strange behavior may occur.

Severe Hypothermia is when the core temperature drops below 31 degrees Celsius. Skin is cold, may be bluish-gray in color, eyes may be dilated. The patient is very weak, displays a marked lack of coordination, slurred speech, appears exhausted, may appear to be drunk, denies there is a problem and may resist help. There is a gradual loss of consciousness. There may be little or no apparent breathing, the patient may be very rigid, unconscious, and may appear dead.

Simple methods for treating hypothermia have been known since very early times. Such methods include wrapping the patient in blankets, administering warm fluids by mouth, and immersing the patient in a warm water bath. Even these simple methods may be effective if the hypothermia is not too severe. These simple methods are limited in their effectiveness however. Wrapping the patient in blankets ultimately depends on the patient's own production of heat to rewarm his body. In even moderate cases of hypothermia, or in the case of an ill or injured patient, the patient may simply be too weak or exhausted to produce sufficient heat. Oral administration of a warm fluid requires that the patient be conscious and capable of swallowing the fluid. Since loss of consciousness occurs early in hypothermia, this method is also limited to moderate cases. Immersion of the patient in a warm water bath is often simply impractical. For example, immersion of a patient undergoing surgery would obviously be undesirable. Furthermore, the immersion technique is time consuming and may be ineffective in that it requires the transmission of warmth from the patient's skin surface into the body core before the benefit of the warmth can be realized. Other devices allow for the direct warming of a patient's blood. These methods involve removing blood from the patient, warming the blood in external warming equipment, and delivering the blood back into the patient. While such methods are much more effective than any of the simple methods previously described, they are disadvantageous for other reasons. First, the apparatus involved is quite cumbersome. Second, some danger is involved in even the temporary removal of significant quantities of blood from an already weakened patient. In fact, a further drop in body temperature is often experienced when blood is first removed for warming in the external apparatus. Finally, special catheters are used for the direct warming of a patient's blood. However, those catheters require a trained staff to insert the device to a central blood vessel of the patient and those physicians are available only in specific units and not in the ambulance or even not always in the emergency room. Those instruments are also very expensive and thus are not available for every caregiver.

Hyperthermia is a condition of abnormally high body temperature. It may result from exposure to a hot environment, overexertion, or fever. Body core temperatures can range from 38-41 degrees Celsius due to fever and may be substantially higher in cases of exposure and overexertion. Like hypothermia, hyperthermia is a serious condition and can be fatal. Also like hypothermia, simple methods for treating hyperthermia, for example, immersion of the patient in a cool water bath or administration of cool fluids, have long been known. In general, it is as hard to treat hyperthermia as it is to treat hypothermia.

Recent medical reports have described the use of controlled hypothermia as a means to reduce oxygen consumption of tissue, such as the heart muscle and the brain during decreased perfusion that occurs as a result of myocardial infarction and ischemic stroke (respectively), which leads to reduced damage and decrease of the infarcted area. Medical reports have also described the prophylactic use of controlled hypothermia during cardiac surgery or interventional cardiology procedures for reducing damage from ischemia and/or embolization in the heart and brain during and after the procedure.

The following patents and patent applications describe apparatus and methods for affecting a patient's body temperature. These, and all other patents and patent applications referred to herein, are hereby incorporated by reference in their entirety.

WO03059425 Method for altering the body temperature of a patient using a nebulized mist—Body temperature reducing method involves administering nebulized mist at temperature below body temperature of patient until patient's temperature is reduced.

US20030136402 Method for altering the body temperature of a patient using a nebulized mist—Body temperature reducing method involves administering nebulized mist at temperature below body temperature of patient until patient's temperature is reduced.

U.S. Pat. No. 6,303,156 Noninvasive method for increasing or decreasing the body temperature of a patient—Increasing or decreasing body temperature for treating e.g. hemorrhagic shock comprises administering oxygen and sulfur hexafluoride gas mixture by hyperventilation.

EP1089743 Composition containing sulfur hexafluoride and oxygen, for increasing or decreasing the body temperature of a patient—Increasing or decreasing body temperature for treating e.g. hemorrhagic shock comprises administering oxygen and sulfur hexafluoride gas mixture by hyperventilation.

WO9966938 Composition containing sulfur hexafluoride and oxygen, for increasing or decreasing the body temperature of a patient—Increasing or decreasing body temperature for treating e.g. hemorrhagic shock comprises administering oxygen and sulfur hexafluoride gas mixture by hyperventilation.

US20030066304 Method for inducing hypothermia—Hypothermia-inducing treatment method for patient in cardiac arrest involves performing continuous administering of phase-change particulate slurry to patient in cardiac arrest until state of hypothermia is induced to patient.

U.S. Pat. No. 6,547,811 Method for inducing hypothermia—Improvement of a cardiac arrest patient's outcome by pre-hospital administration of a phase-change particulate slurry internally until a state of hypothermia is induced.

WO0108593 Method for inducing hypothermia—Improvement of a cardiac arrest patient's outcome by pre-hospital administration of a phase-change particulate slurry internally until a state of hypothermia is induced.

US20030131844 Inducing hypothermia and rewarming using a helium-oxygen mixture—Composition useful for treating ischemic event by inducing hypothermia comprises a gas mixture comprising helium and oxygen having temperature significantly different than normal human body temperature.

WO03047603 Breathable gas mixtures to change body temperature—Composition useful for treating ischemic event by inducing hypothermia comprises a gas mixture comprising helium and oxygen having temperature significantly different than normal human body temperature.

U.S. Pat. No. 5,755,756 Hypothermia-inducing resuscitation unit—Hypothermia inducing apparatus for cardio pulmonary resuscitation in accident—has stretcher and liquid oxygen and carbon dioxide sources that are maintained in movable state to transport patient from trauma site to hospital.

U.S. Pat. No. 6,149,624 Apparatus and method for the rapid induction of hypothermic brain preservation—Assembly for inducing rapid hypothermic brain preservation using a liquid pulmonary lavage, comprises a fluid reservoir, a heat exchanger for cooling the pulmonary lavage, a means for circulating the lavage and an effluent reservoir.

WO0018459 Mixed-mode liquid ventilation gas and heat exchange—Gas and heat exchange method in lungs for treatment of hypothermic pathologies, involves mixing oxygenated liquid comprising perfluorocarbon and gas such as helium.

U.S. Pat. No. 6,582,457 Method of controlling body temperature while reducing shivering—Method for controlling body temperature below set point, for reducing shivering, involves sensing temperature, generating signal, controlling temperature based upon signal and administering agent.

U.S. Pat. No. 6,572,638 Method of controlling body temperature while inhibiting thermoregulatory responses—Controlling body temperature while inhibiting thermoregulatory response, involves controlling temperature of patient's body using heat exchange device, and administering anti-thermoregulatory response agent to the patient.

SUMMARY OF THE INVENTION

The present invention provides a method and apparatus for controlling a patient's body temperature and in particular for inducing therapeutic hypothermia. Various embodiments of the system are described. The system includes: a source of breathing gas, which may be in the form of a compressed breathing gas mixture; a heat exchanger or other heating and/or cooling device; and a breathing interface, such as a breathing mask or tracheal tube. Optionally, the system may include additional features, such as a mechanical respirator, a nebulizer for introducing medication into the breathing gas, a body temperature probe and a feedback controller. The system can use air or a specialized breathing gas mixture, such as $He/O_2$ or $SF_6/O_2$ to increase the heat transfer rate. In addition, the system may include an ice particle generator for introducing fine ice particles into the flow of breathing gas to further increase the heat transfer rate.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Figure 1:
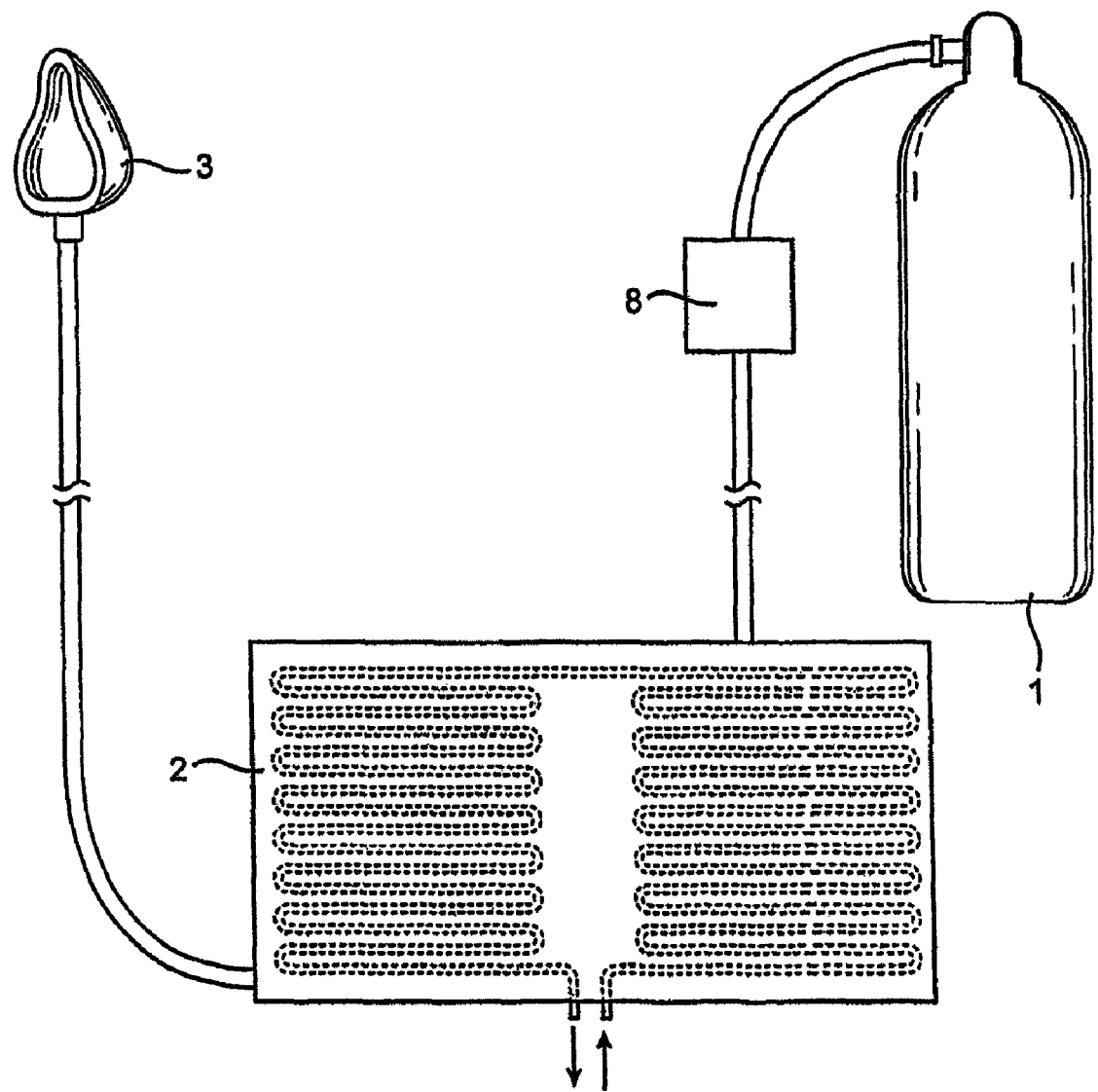
FIG. 1 is a schematic diagram of a first embodiment of the apparatus for inducing therapeutic hypothermia using a source of compressed breathing gas and a heat exchanger.

The present invention provides methods and apparatus for modifying and controlling a patient's body temperature. According to the present invention the patient will be wearing a mask that will provide the patient with the breathing mixture. Alternatively, the patient may be intubated with a tracheal tube. The system will work with patients who breathe spontaneously as well as patients who are mechanically ventilated. The respiratory gas may be air or a special gas mixture that includes oxygen (about 20% concentration or more) and a gas with a high heat capacity (Cp) for more effective heat exchange. The mixture can be regular or purified air, or air with a higher concentration of oxygen (from 20 to 100%). A different possible mixture will be oxygen and helium, which has been proven to be safe and is used by divers and for treatment of patients with airway disease such as asthma (for example HELIOX, which is 20% oxygen and 80% helium). The specific heat capacity for helium is much higher than the specific heat capacity for air, thus using a helium/oxygen mixture will improve the heat flow rate and will enable a much more effective way of changing the patient's temperature. Alternatively or in addition, the mixture may include sulfur hexafluoride $SF_6$, which is a dense, nontoxic gas that has a much higher specific heat capacity than air. The invention does not limit the gas mixture and other combinations of gasses that are biocompatible and safe that will serve for the temperature exchange may optionally be used.

Other gases may be added to the mixture. For example, carbon dioxide ($CO_2$) may be added to the gas mixture to help regulate the patient's respiration rate. A $CO_2$ partial pressure will induce hyperventilation, i.e. cause the patient to breathe faster, which will increase the gas mixture flow rates and thus improve the rate of heat transfer within the patient's lungs. Conscious patients may be asked to hyperventilate to increase the gas mixture flow rate. Alternatively, patients may be caused to hyperventilate through use of positive and negative pressure, such as when a mechanical ventilator or similar apparatus is used. $CO_2$ may be added to ensure that proper levels of $CO_2$ and $O_2$ are maintained in the patient's blood. A higher concentration of $CO_2$ in the breathing mixture will help to prevent hypocapnia that may result from hyperventilation. Other gases, for example nitrous oxide, can also be added to the breathing gas mixture.

The invention will also enable controlling the pressure of the inhaled gas. Pressurizing the gas will further improve the gas mixture mass flow rate, and hence the heat transfer rate. The system will be able to pressurize the inhaled gas to what is known to be safe to the patient (for example 1.5-2 atmospheres). Alternatively, the system may pulse the gas, i.e. vary the pressure continuously from high to low, which will help mixing the gas and improve the heat transfer rate.

Alternatively or in addition, jets of air (high pressure boluses of gas) delivered through the mask or through a tracheal tube will also help mixing the gas and improve the heat transfer rate.

The invented device will also control the humidity of the inhaled gas. Changing the content of water in the inhaled gas could influence the heat flow rate.

The device will also record the patient's temperature using any known way of measuring a patient's temperature (like a probe that will be inserted to the patient's rectum or a probe that will check the patient's skin temperature but will be separated from the room temperature by a bandage that can isolate it effectively, or using IR to measure tympanic temperature or any other way to check temperature). The device will use the recorded temperature as a feedback and will adjust the temperature of the inhaled gas according to the desired patient temperature.

The gas will be cooled or heated using any known way of cooling or heating. For example, a system of heat exchangers that will enable heat exchange between the gas outside the heat exchanger and liquid or gas inside the heat exchangers. Another option is to use an electric heater/cooler. Another option is to use a heat pump. Another means of cooling the gas will be that the gas will be pressurized inside special pressure resistant containers/bottles. When gas is released from a high pressure to a lower pressure heat is released and the temperature of the gas drops.

Since the rate of heat transfer is affected by the difference of the temperatures of the gas and the patient, the device will be configured to deliver gas at a very low temperature that will be proven to be safe.

The device will be used by the first aid giver, such as paramedics in an ambulance or medical team outside the hospital, by a team in the emergency room or any other place where this treatment is necessary. Advantages of the system include ease of operation and the fact that it could be operated with minimal training. Thus treatment of the patient can begin much sooner after a heart attack, stroke or other event compared to other more invasive methods that must be performed in the emergency room or in the cath lab. Rapid treatment for these conditions has been shown to improve patient outcomes by reducing ischemic damage and necrosis in the affected tissue.

The cold/hot gas will be in contact with the huge surface area of the lungs. The temperature of the blood in the lungs will change and this blood will flow to the left heart and there will change the temperature of the heart tissue. From the left ventricle some of the blood flows to the coronary arteries (where it will continue to influence the temperature of the tissue and change the metabolism and the oxygen consumption). In the case of myocardial infarction, the effect of this chilled blood flowing directly into the coronaries is especially beneficial. The blood also flows from the left heart to the entire body and there it will also change the temperature as desired. In the case of stroke, a portion of the cooled blood will flow to the brain, cooling the tissue and reducing the metabolism and the oxygen consumption, which will reduce ischemic damage to the brain.

The system will potentially be able to use drugs like bronchodilators and local (inhaled) vasodilators or any other medications that will increase the blood flow to the lungs for better heat transfer and prevent bronchoconstriction from the cold breathing mixture. The system will also potentially be able to be used in conjunction with drugs that encourage perspiration, peripheral vasodilators and drugs that reduce or eliminate shivering. Other medications that can be administered by inhalation may be added to the breathing mixture, for example using a nebulizer.

Figure 2:
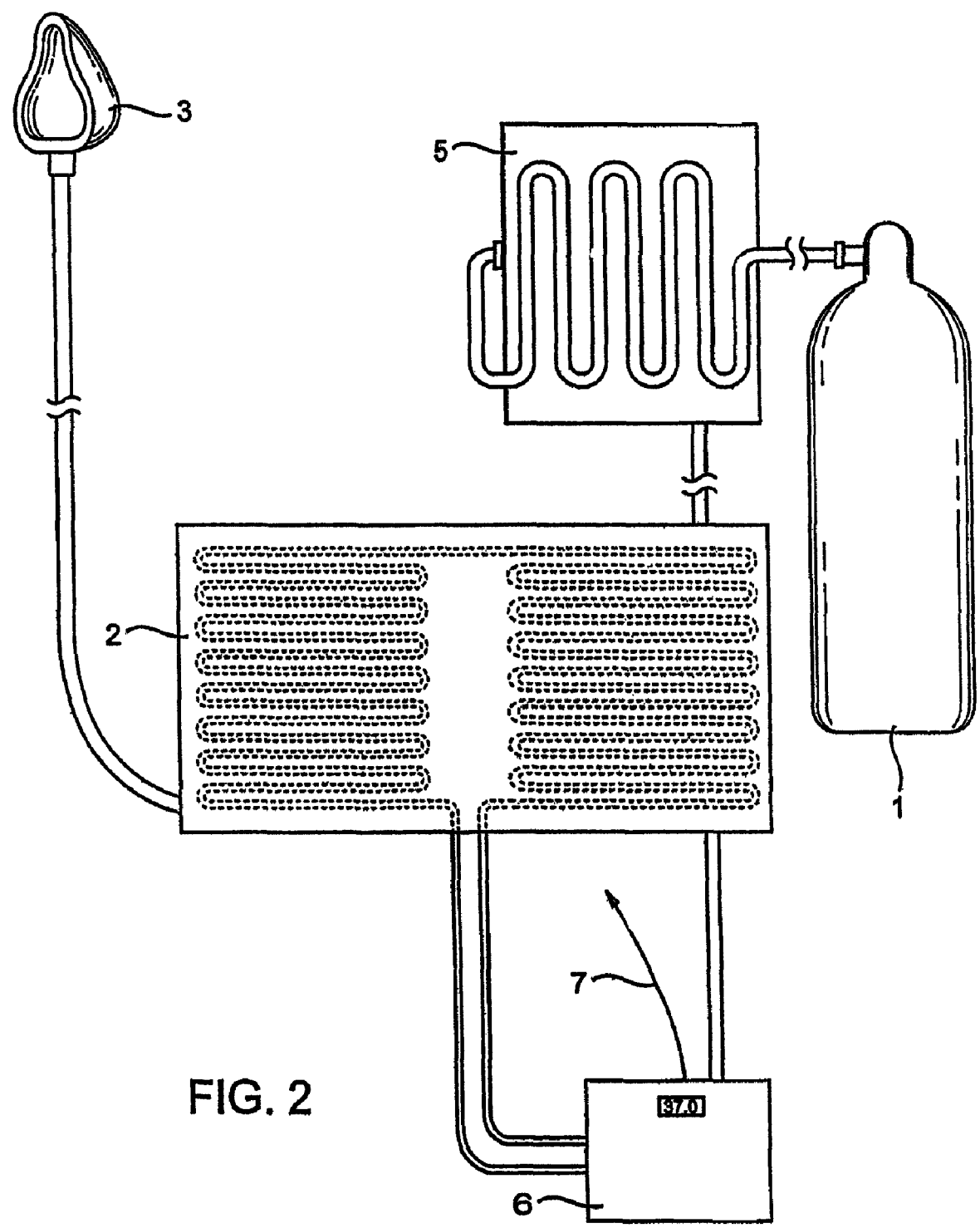
FIG. 2 is a schematic diagram of a second embodiment of the apparatus for inducing therapeutic hypothermia using adiabatic cooling of a compressed breathing gas as an adjunct to the heat exchanger.

FIGS. 1-2 illustrate various embodiments of an apparatus for controlling a patient's temperature and inducing therapeutic hypothermia. These examples are not intended to be limiting. The features of these embodiments can be combined and arranged in other configurations to form other embodiments of the invention.

FIG. 1 is a schematic diagram of a first embodiment of the apparatus for inducing therapeutic hypothermia using a source of compressed breathing gas and a heat exchanger. The system includes a supply of compressed breathing gas stored in a pressurized container 1. The gas is delivered though a heat exchanger 2 or other heating and/or cooling apparatus to the mask 3 that the patient is using. Optionally, the system includes a humidifier 8 to humidify the gas in order to improve heat transfer.

FIG. 2 is a schematic diagram of a second embodiment of the apparatus for inducing therapeutic hypothermia using adiabatic cooling of a compressed breathing gas as an adjunct to the heat exchanger. The system includes a supply of compressed breathing gas 1 and a heat exchanger 2 where the heat is exchanged with fluid located inside the heat exchanger. The temperature of the fluid in the heat exchanger is changed and monitored by a separate heating and/or cooling device 6. The system includes a device 5 that uses the cold temperature that results from depressurizing the gas to help cool the patient 5. A temperature sensor probe 7 records the patient's temperature and a feedback controller associated with the heating and/or cooling device 6 uses it as feedback to determine the desired temperature of the breathing gas.

Figure 3:
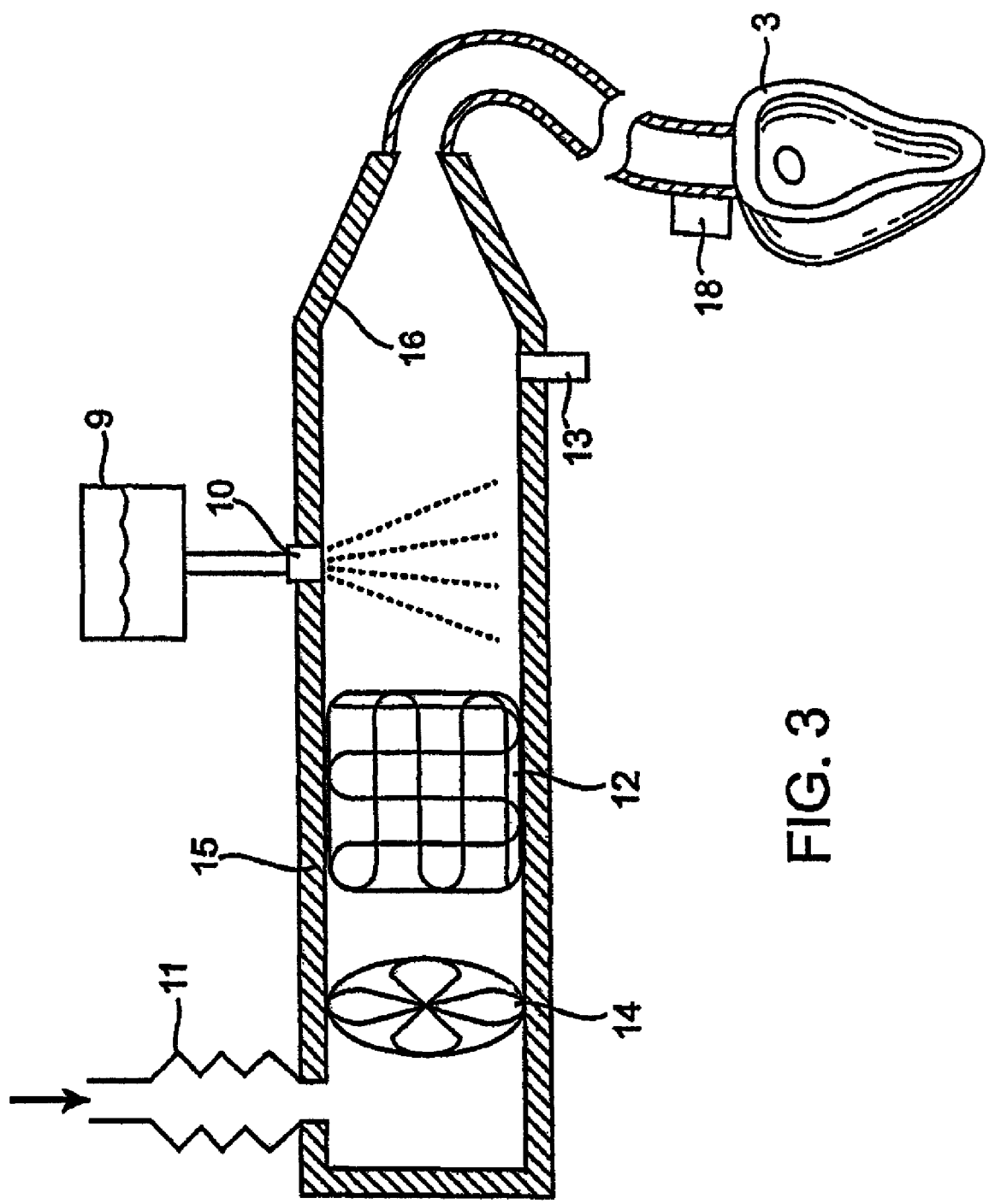
FIG. 3 is a schematic diagram of a third embodiment of the apparatus for inducing therapeutic hypothermia that includes a fluid source and a fluid injector for creating ice particles or a frozen mist to enhance heat capacity of the breathing gas mixture.

FIG. 3 is a schematic diagram of a third embodiment of the apparatus for inducing therapeutic hypothermia that includes a fluid source 9 and a fluid injector 10 for creating ice particles or a frozen mist to enhance the heat capacity of the breathing gas mixture. The fluid source 9 will preferably contain normal saline solution (0.9% NaCl) or any other desired solution, so that it will be isotonic with the patient's blood. Alternatively plain water, e.g. distilled water, may be used. If plain water is used, NaCl may be added to the breathing mixture in the proper amount to maintain an isotonic concentration or administered to the patient orally or via another route. Optionally, the system may be connected to a mechanical respirator 11, particularly for patients who are not breathing spontaneously. The system may use air or one of the specialized gas mixtures described above. The incoming breathing gas is passed through a heat exchanger 12 to cool it to a temperature below the freezing point of the injected fluid (below 0 degrees Celsius for water and below −0.52 degrees Celsius for normal saline solution). The heat exchanger can utilize a refrigeration cycle, a reversible heat pump, a thermoelectric heater/cooler, dry ice, liquid nitrogen or other cryogen, or other known heater/cooler to achieve the desired temperature.

A fine spray of fluid droplets is injected into the cooled breathing gas mixture to form a frozen mist of fine ice particles. The fluid injector 10 may include an orifice-type atomizer or an ultrasonic atomizer to achieve a small and uniform droplet size. An ultrasonic atomizer will typically produce droplets (and hence ice particles) with a size in the range of 2 to 5 microns, which can easily be suspended in the moving flow of the breathing gas mixture. However, larger or smaller droplets and ice particles will also be effective. Optionally, the system may include a screen or filter downstream from the ice particle generator to limit the size of ice particles delivered to the patient. The amount of ice particles added to the breathing gas mixture is preferably in the range of 0 to 5 liters per hour (measured as the volume of fluid injected to produce the frozen mist.) A flow rate of ice particles in the range of 0.25 to 1 liters per hour is currently thought to be sufficient for rapidly achieving hypothermia in an adult human patient. Due to the heat of fusion (the heat required to effect a phase change from liquid water to ice), the incoming breathing gas may need to be cooled to a temperature significantly below the freezing point to achieve effective freezing of the fluid droplets. In addition, it may be helpful to pre-cool the fluid to a temperature close to freezing before it is injected into the breathing gas. An additional heat exchanger may be included for this purpose. Optionally, the fluid injection can be timed with the pulsatile flow of breathing gas. Optionally, a fan 14 may be included to constantly circulate the breathing gas within the system to avoid the fluid droplets and ice particles from settling out of the breathing gas. Preferably, the system is insulated 15 to avoid condensation or frost formation on the exterior of the conduit and to prevent heat exchange with the ambient environment. Optionally, the interior surface of the conduit may be coated with Teflon or a hydrophobic coating 16 to avoid fluid or ice from accumulating on the interior surface. A drain 13 is provided for removing any fluid that accumulates within the system. Optionally, the system may include a nebulizer 18 for introducing medications into the flow of breathing gas.

Other methods may be used for adding the ice particles to the breathing gas mixture. For example, solid ice may be ground or shaved into small particles and added to the flow of the breathing gas mixture. Alternatively, small ice particles can be produced and stored ahead of time and added to the flow of the breathing gas mixture, for example using a screw-type metering device, a vibratory feeder, or any other means of controlling the quantity of ice particles delivered into the breathing mixture. Water droplets and compressed gas, for example carbon dioxide, can be release together so that the adiabatic cooling of the expanding gas will freeze the water droplets into ice particles. The resulting mixture of expanded gas and frozen particles can be mixed with air and/or with oxygen and other gases to produce the desired breathing gas mixture. Alternatively or in addition, the system may utilize other types of frozen particles, for example dry ice particles, to enhance the heat capacity of the breathing gas mixture.

The system is connected to a breathing mask 3 or tracheal tube for the patient to breathe through. The frozen mist is carried into the patient's lungs by the breathing gas. The ice particles melt within the patient's lungs providing a high rate of heat transfer for cooling the lungs and the blood that flows through it. A heat transfer analysis outlined below indicates the beneficial effect of the frozen mist on the heat transfer rate. The system is used in this manner until the desired degree of hypothermia is achieved. Once hypothermia has been achieved, the rate of heat transfer can be reduced by reducing the quantity of ice particles delivered and the temperature of the heat exchanger can be adjusted to maintain body temperature. One advantage of this embodiment of the system is that, because of the high heat transfer rate provided by the ice particles, an extremely low temperature will not be needed for effective cooling of the patient thereby mitigating the risk of freezing damage to the patient's lungs. After the need for protective hypothermia has passed, the system may be used for rewarming the patient to normothermia.

The amount of fluid that forms in the lungs from the melting of the ice particles will be easily tolerated by the patient. An adult human with good lung function can readily clear 1 liter per hour of fluid from the lungs through normal processes. Thus, a flow rate of ice particles in the range of 0.25 to 1 liters per hour will be readily tolerated for an extended period of several hours. Higher flow rate of ice particles, up to 5 liters per hour, can be tolerated for shorter periods. If desired, positive pressure ventilation may be used to help drive the fluid from the lung passages into the surrounding tissue and from there into the bloodstream. In addition, diuretics or other medications to treat pulmonary edema may be administered to the patient to help eliminate excess water if needed.

Anti-shivering agents and/or anti-thermoregulatory response agents may be administered to the patient to assist in achieving the desired degree of hypothermia. Alternatively or in addition, external warming, such as with a warm air blanket or electric blanket, may be applied to reduce shivering while internal hypothermia is maintained. Regional heating of selected portions of the patient's body may be used to control shivering and/or to "trick" the body's thermoregulatory responses.

For increased heating or cooling effect, the apparatus and methods described herein can be used in combination with any known body temperature control systems, such as those described in the patents cited above. Alternatively or in addition, external heating or cooling can be applied to augment the total heat transfer rate. Peripheral vasodilators and/or drugs that encourage perspiration may also be administered to the patient to increase heat loss through the skin.

Analysis of the Effects of Adding Ice Particles to Breathing Mixture for Control of Patient Body Temperature Baseline calculations and initial animal studies showed that cooling the breathing mixture supplied to a patient will lower core body temperature over time. Initial calculations for various mixtures of gases indicate that the rate of heat transfer from the patient to the breathing mixture will range from a low of about 10 Watts for the case of an $He/O_2$ mixture at atmospheric pressure with an initial temperature of $-30.$degree. C. and a volumetric flow rate of 20 l/min, to a high of 117 Watts for the case of an $air/CO_2$ breathing mixture at 2 atm pressure with an initial temperature of $-30.$degree. C. and a volumetric flow rate of 100 l/min.

An analysis of the addition of ice particles to the mixture shows a significant contribution to the heat transfer rate. The precise level of fluid addition that is tolerable to the patient is as yet unknown, so analyses were performed for ice particle addition rates ranging from 0.25 to 5 liters/hour. The ice particles were assumed to be small in size, and to have an initial temperature of $-30.$degree. C. Heating of the ice particles was broken down into 3 steps: 1) heating the solid ice from $-30.$degree. C. to $0.$degree. C., 2) causing a solid-to-liquid phase change at $0.$degree. C., and 3) heating the liquid water from $0.$degree. C. to $37.$degree. C. For the various rates of addition of ice particles, the following heat transfer rates resulted:

TABLE 1

| Rate of Ice Particle Addition (liters/hour) | Power to Heat Ice from −30° C. to 0° C. (W) | Power for Solid/Liquid Phase Change (W) | Power to Heat Liquid from 0° C. to 37° C. (W) | Total Power (W) |
|---|---|---|---|---|
| 0.25 | 3.8 | 21.5 | 10.0 | 35.2 |
| 0.5 | 7.5 | 42.9 | 19.9 | 70.4 |
| 1 | 15.1 | 85.9 | 39.8 | 140.8 |
| 2.5 | 37.7 | 214.7 | 99.6 | 352.1 |
| 5 | 75.4 | 429.5 | 199.2 | 704.1 |

The calculations assume that the ice is mixed with air at atmospheric pressure, initially at $-30.$degree. C., with a volumetric flow rate of 20 l/min.

Figure 4:
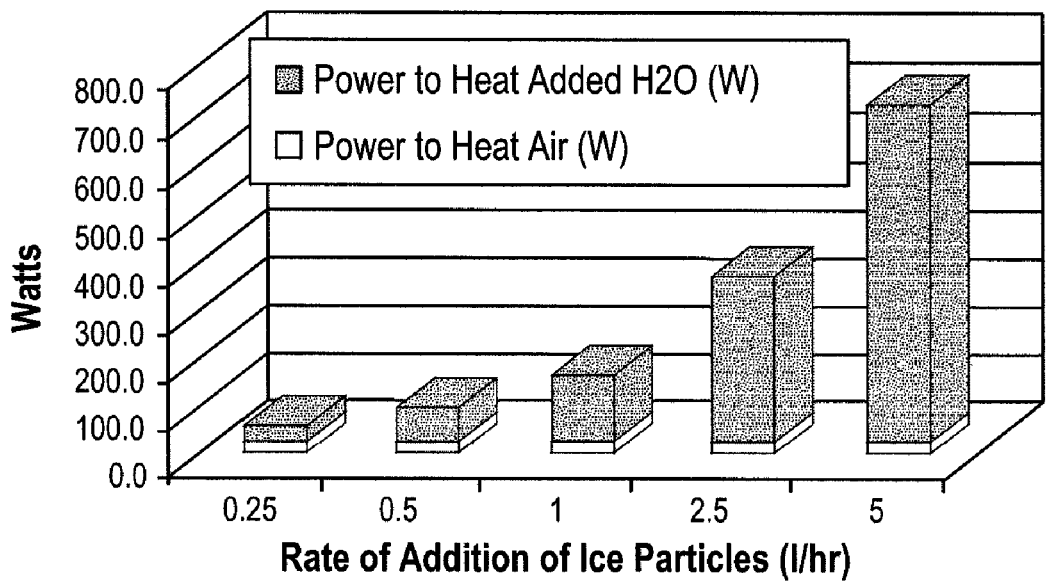
FIG. 4 is a bar graph showing the heat removed from the body (Watts) as a function of the rate of ice particles added to the breathing mixture (1/hr).

FIG. 4 is a bar graph showing the heat removed from the body (Watts) as a function of the rate of ice particles added to the breathing mixture (1/hr).

Figure 5:
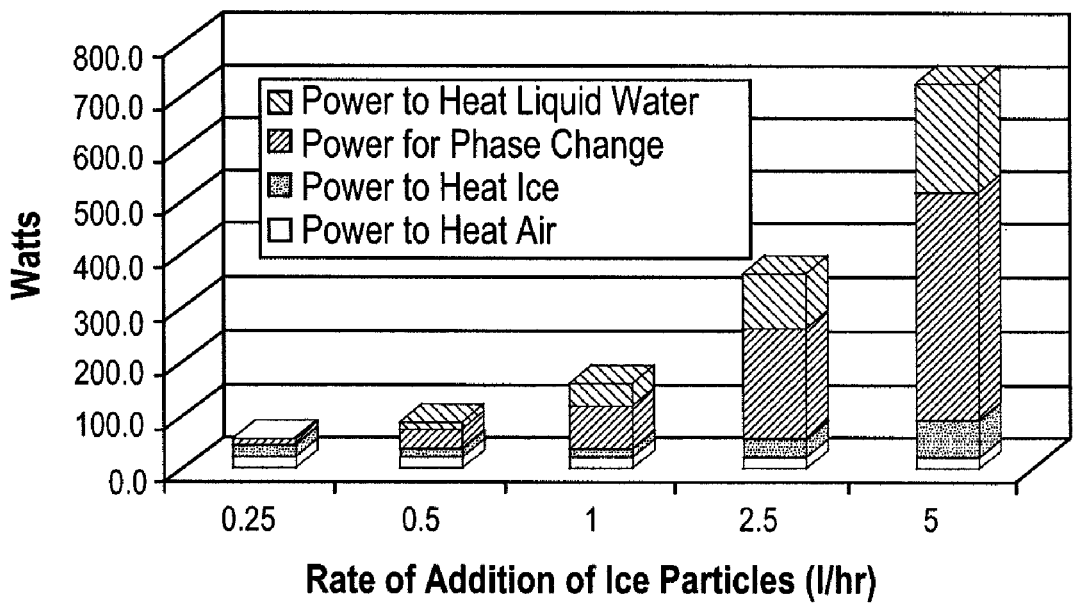
FIG. 5 is a bar graph showing a more detailed breakdown of the heat removed from the body (Watts) as a function of the rate of ice particles added to the breathing mixture (1/hr).

FIG. 5 is a bar graph showing a more detailed breakdown of the heat removed from the body (Watts) as a function of the rate of ice particles added to the breathing mixture (1/hr). The analysis shows that the addition of ice particles will have a significant effect, and that the majority of the heat transfer is contributed by the phase change of the ice to liquid water, and that the smallest contribution comes from the power required to heat the ice to $0.$degree. C.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method for inducing therapeutic hypothermia in a patient, comprising:
    cooling a breathing gas mixture;
    injecting a fluid into the cooled breathing gas mixture to form a frozen mist of fine ice particles in the cooled breathing gas mixture;
    delivering the cooled breathing gas mixture to an airway of the patient.

2. The method of claim 1 wherein the airway comprises a nasal airway of the patient.

3. The method of claim 1 wherein the airway comprises a lung of the patient.

4. The method of claim 1 wherein the airway comprises a lung and a nasal airway of the patient.

5. The method of claim 1 wherein the cooled breathing gas mixture is delivered to the airway of the patient through a breathing mask.

6. The method of claim 1 further comprising the step of injecting a drug into the cooled breathing gas mixture.

7. The method of claim 1 wherein fluid is injected into the cooled breathing gas mixture with a fluid injector.

8. The method of claim 1 wherein fluid is injected into the cooled breathing gas mixture with an atomizer.

9. The method of claim 1 wherein fluid is injected into the cooled breathing gas mixture with a nebulizer.

10. A method for inducing therapeutic hypothermia in a patient, comprising:
    forming a breathing gas mixture;
    cooling the breathing gas mixture;
    injecting a fluid into the cooled breathing gas mixture to form a frozen mist of fine ice particles in the cooled breathing gas mixture;
    delivering the cooled breathing gas mixture to an airway of the patient.

11. The method of claim 10 wherein the airway comprises a nasal airway of the patient.

12. The method of claim 10 wherein the airway comprises a lung of the patient.

13. The method of claim 10 wherein the airway comprises a lung and a nasal airway of the patient.

14. The method of claim 10 wherein the cooled breathing gas mixture is delivered to the airway of the patient through a breathing mask.

15. The method of claim 10 further comprising the step of injecting a drug into the cooled breathing gas mixture.

16. The method of claim 10 wherein fluid is injected into the cooled breathing gas mixture with a fluid injector.

17. The method of claim 10 wherein fluid is injected into the cooled breathing gas mixture with an atomizer.

18. The method of claim 10 wherein fluid is injected into the cooled breathing gas mixture with a nebulizer.

19. The method of claim 10 wherein the forming step comprises forming the breathing gas mixture from a gas mixture that includes oxygen and a gas with a high heat capacity.

20. The method of claim 10 wherein the forming step comprises forming the breathing gas mixture from a gas mixture that includes oxygen and helium.

21. The method of claim 10 wherein the forming step comprises forming the breathing gas mixture from a gas mixture that includes oxygen and carbon dioxide.

22. The method of claim 10 wherein the forming step comprises forming the breathing gas mixture from a gas mixture that includes sulfur hexafluoride.

23. The method of claim 10 further comprising pressurizing the breathing gas mixture.

\* \* \* \* \*